(12) United States Patent
Aonuma

(10) Patent No.: US 6,812,022 B1
(45) Date of Patent: Nov. 2, 2004

(54) BACILLUS SUBTILIS TAKEMI AND COMPOSITIONS THEREOF

(75) Inventor: Takemi Aonuma, Miyagi (JP)

(73) Assignee: Gold Kosan Co., Ltd., Miyagi (JP)

( * ) Notice: Subject to any disclaimer, the term of this patent is extended or adjusted under 35 U.S.C. 154(b) by 0 days.

(21) Appl. No.: 09/889,263

(22) PCT Filed: Jan. 14, 1999

(86) PCT No.: PCT/JP99/00117

§ 371 (c)(1),
(2), (4) Date: Oct. 16, 2001

(87) PCT Pub. No.: WO00/42169

PCT Pub. Date: Jul. 20, 2000

(51) Int. Cl.$^7$ ............................ C12N 1/20; A01N 63/00
(52) U.S. Cl. ................................ 435/252.5; 424/93.46; 426/61; 426/52; 426/53
(58) Field of Search .................... 435/252.5; 424/93.46; 426/61, 52, 53

(56) References Cited

U.S. PATENT DOCUMENTS

| | | | | |
|---|---|---|---|---|
| 4,278,696 A | * | 7/1981 | Magnolato | 426/422 |
| 5,215,747 A | * | 6/1993 | Hairston et al. | 424/93.462 |
| 5,531,898 A | | 7/1996 | Wickham | |
| 5,614,188 A | * | 3/1997 | Urano et al. | 424/93.46 |
| 5,972,689 A | * | 10/1999 | Cook et al. | 435/252.31 |
| 6,060,051 A | * | 5/2000 | Heins et al. | 424/93.462 |

FOREIGN PATENT DOCUMENTS

| | | |
|---|---|---|
| EP | 0 287 699 A | 11/1988 |
| JP | 63304990 | 12/1988 |
| JP | 3228689 | 10/1991 |
| JP | 3236771 | 10/1991 |
| JP | 8-154616 | 6/1996 |
| WO | WO 96/39840 | 12/1996 |
| WO | WO 98/50422 | 11/1998 |

OTHER PUBLICATIONS

Shojiro, Horiguchi, *Patent Abstracts of Japan*, vol. 015, No. 189, May 1991.

Hoffmann, T. et al., "The anaerobic life of *Bacillus subtilis*: Cloning of the genes encoding the respiratory nitrate reductase system" *FEMS Microbiology Letters*, vol. 131, No. 2, 219–225, 1995.

Takenori, Okudaira, *Patent Abstracts of Japan*, vol. 1997, No. 5, May 1997.

RU 2122026–C, "Volg Anti–Plague Res Inst", Nov. 20, 1998.

Bashan, Y., "Inoculants of plant growth–promoting bacteria for use in agriculture", *Biotechnol. Adv.*, vol. 16, No. 4, 729–770, 1998.

* cited by examiner

*Primary Examiner*—Irene Marx
(74) *Attorney, Agent, or Firm*—Gray Cary Ware & Freidenrich, LLP

(57) ABSTRACT

Microorganisms of the genus Bacillus that are capable of reducing nitrates and contain chitin and/or chitosan in their cell walls are provided. The microorganism of the invention can be used for improving soil, for treating organic waste by fermentation, for fermenting soybeans, and for reducing bitterness. The microorganism of the invention can also be used as a feed additive or a good additive. Further, the microorganism of the invention has an anti-microbial effect.

6 Claims, 1 Drawing Sheet

FIG. 1

[GENETYX-MAC : Nucleotide Sequence Homology Data]

1st Nucleotide Sequence
   File Name          : coffee 16S rRNA   (positions 1037-1406 of
   Sequence Size     : 326                Bacillus subtilis takemi 16S rRNA)

2nd Nucleotide Sequence
   File Name          : Bacillus subtilis (Accession No. D84213)
   Sequence Size     : 15467

Unit Size to Compare = 4
   Pick up Location    = 1

[92.7% / 331 bp]     OPT.Score : <   1117 >

```
    1' GAGATGTT-GGTTAAGTCCCGCGACGAG-GCNACCCTTG-TNTNAGTNGCCAGCAATTCAG-
       ******** ******************* **.******* *.*.***.****** ******
 1700" GAGATGTTGGGTTAAGTCCCGCAACGAGCGCAACCCTTGATCTTAGTTGCCAGC-ATTCAGT

59' TNGGCANTNTAAAGTGACTGCC-GTGACAAGCCGGAGGAAAGGTGGGAATGACGTCAAATCA
       *.***.*.*** ********* ******* ******* ******* ***************
 1761" TGGGCACTCTAAGGTGACTGCCGGTGACAAACCGGACG-AAGGTGGGGATGACGTCAAATCA

120' TCATGCCCCTATACGACNTGGGCTACACACGTGCTACCATGGACAGAACAAAGGGCAGCGAA
       ********* ** ***.******************** **********************
 1822" TCATGCCCCT-TATGACCTGGGCTACACACGTGCTACAATGGACAGAACAAAGGGCAGCGAA

182' ACCGCGAGGTTAAGCCAATCCCACAAATCTGTTCTCAGTTCGGATCGCAGTNTGCAACTTCG
       ************************************************ .****** ***
 1883" ACCGCGAGGTTAAGCCAATCCCACAAATCTGTTCTCAGTTCGGATCGCAGTCTGCAAC-TCG

244' ACTGCGTGAAGCTGGAATCGCTAGTAATCGCGGATCAGCATGCCGCGGTGAATACGTTCCCG
       ************************************************************
 1944" ACTGCGTGAAGCTGGAATCGCTAGTAATCGCGGATCAGCATGCCGCGGTGAATACGTTCCCG

305' GGCCTTGTACACACCGCCCGT
       *********************
 2006" GGCCTTGTACACACCGCCCGT
```

BACILLUS SUBTILIS TAKEMI AND COMPOSITIONS THEREOF

This application was filed under 35 USC 371 as the national phase of PCT/JP99/00117 filed Jan. 14, 1999.

TECHNICAL FIELD

The present invention relates to microorganisms of novel species and methods for using the same. More specifically, the present invention relates to microorganisms of novel species belonging to the genus Bacillus and methods for using the same.

TECHNICAL BACKGROUND

Mankind has utilized various microorganisms to date. For example, a wide variety of foods such as alcoholic drinks, fermented seasonings (e.g. soybean paste and soy sauce), fermented dairy products (e.g. cheese and yogurt) and bread have been produced using actions of microorganisms. In addition, microorganisms have also been utilized in the manufacturing of pharmaceuticals and agricultural chemicals, in the production of energy sources such as alcohol and methane, in the treatment of waste and wastewater, and so forth.

The technology of using functions of living things (especially microorganisms) in industrial processes, which is called biotechnology, is developing remarkably in these days. The discovery of novel, useful microorganisms contributes to the advance of biotechnology.

Under circumstances, it is an object of the present invention to provide novel, useful microorganisms.

It is another object of the present invention to provide methods of use of the microorganisms.

DISCLOSURE OF THE INVENTION

The present inventors have isolated from soil a microorganism of a novel species having a smell of coffee. Thus, the present invention has been achieved. The present invention provides microorganisms belonging to the genus Bacillus that are capable of reducing nitrates and contain chitin and/or chitosan in their cell walls. The microorganism of the invention may have a smell of coffee. The microorganism of the invention may be a microorganism belonging to *Bacillus subtilis*. As one example of the microorganism of the invention, *Bacillus subtilis takemi* (FERM BP-6589) may be given.

The present invention also provides a method for improving soil using the microorganism, and a composition for improving soil comprising the microorganism.

Further, the present invention provides a method for treating organic waste by fermentation using the microorganism, and a composition for treating organic waste by fermentation comprising the microorganism.

Further, the present invention provides a method for fermenting soybeans using the microorganism, and soybeans that have been fermented using the microorganism.

The present invention also provides a method of using the microorganism as a feed additive, and a feed additive comprising the microorganism.

The present invention also provides a method of using the microorganism for reducing bitterness, and a composition for reducing bitterness comprising the microorganism. The present invention also provides a method of using the microorganism as a food additive, and a food additive comprising the microorganism.

The present invention also provides a method for inhibiting bacterial growth using the microorganism, and an anti-microbial composition comprising the microorganism. Specific examples of target bacteria of which the growth can be inhibited by the microorganism of the invention include staphylococci, pathogenic *E. coli* O157 and O147, dermatophytes, and bacteria of the family micrococcaceae.

The microorganism of the invention is a bacterium belonging to the genus Bacillus that is capable of reducing nitrates and contains chitin and/or chitosan in its cell walls. The microorganism of the invention may have a smell of coffee. As a specific example of such a microorganism, *Bacillus subtilis takemi* (FERM BP-6589) may be given. This microorganism has been isolated as described below from a soil sample collected in Siberia.

Briefly, 500 $\mu$l of sterilized distilled water was added to 50 mg of a Siberian soil sample, which was then shaken for 30 min to prepare a suspension (presenting a brown color). Using this suspension as a stock solution, 10-2-10-7 dilutions were prepared by 10-fold serial dilution. Then, 100 $\mu$l of each dilution was plated on PDAYC medium (Potato Dextrose Agar medium containing Yeast Extract and Casion) and spread uniformly with a spreader, followed by stationary culture under the condition of all day light and at 20° C. As a result, formation of white colonies was observed in $10^{-2}$–$10^{-4}$ dilutions. It was found that these colonies were not filamentous fungi as a result of microscopic examination. Since all the colonies were white, it was presumed that a single species was growing there. Formation of no colonies was observed in dilutions below $10^{-4}$.

The characters of the isolated microorganism were as summarized below.

TABLE 1

Morphological Characters

| Observation Item | Observation Results |
|---|---|
| Shape and size of cells | |
| Broth agar medium | straight rod-shaped bacteria, 1.2–1.3 $\mu$m × 2.5–3.3 $\mu$m on overnight culture at 30° C. |
| Broth liquid medium | straight rod-shaped bacteria, 0.9–1.2 $\mu$m × 4.6–7.2 $\mu$m on overnight culture at 30° C. |
| Presence/absence of polymorphism | Polymorphism is not observed. |
| Motility | Motility by peritrichous flagella* is observed. |
| Spores | Formation of oval, subcentric spores is observed. Swelling of sporangia is not observed. The size of the spores is 0.9–1.1 $\mu$m × 2.0–2.3 $\mu$m on 5 day culture on broth agar medium at 30. |

TABLE 2

Culture Characteristics in Individual Media

| Medium | State of Growth |
|---|---|
| Broth agar plate | Colonies present a rough surface, and their periphery is wave-like or notched. No luster is observed. |

TABLE 2-continued

Culture Characteristics in Individual Media

| Medium | State of Growth |
|---|---|
|  | Production of neither characteristic colony pigments nor diffusive pigments is observed. |
| Broth liquid medium | Cells grow in the upper part of the medium; formation of a surface membrane is observed; precipitation is not observed. |
| Broth gelatin puncture | Cell growth is observed in the upper part of the medium. Liquefaction is observed. |
| Litmus.milk | Cell growth in the upper part of the medium and liquefaction throughout the medium are observed, but no solidification is observed Production of acid is not observed. |

TABLE 3

Physiological Properties: Part I

| Test Item | Test Results |
|---|---|
| Denitrification reaction | − |
| Methyl red test | + |
| Production of indole | − |
| Production of hydrogen sulfide₁ |  |
| TSI agar | − |
| Lead acetate liquid medium*² | + |
| Assimilation of citrates |  |
| Koser medium | − |
| Christensen medium | + |
| Assimilation of inorganic nitrogen sources |  |
| Nitrates | + |
| Ammonium salts | + |
| Production of pigments | − |
| Urease | + |
| Oxidase | − |
| Range within which cells can grow*³ |  |
| pH    4.5–8.5 |  |
|        (good at 5.5–8.0) |  |
| Temperature   12–51° C. |  |
|        (good at 25–45° C.) |  |
| OF (Hugh-Leifson) o |  |

₁Test media were based on the media described in Takeharu Hasegawa (Ed), "Classification and Identification of Microorganisms (Vol. II)", (1985), GAKKAI SHUPPAN CENTER.
*²Instead of adding lead acetate into the medium, a lead acetate test paper was suspended.
*³Test was performed using meat broth. pH was tested at intervals of 0.5, and temperature was tested at intervals of 1° C.

TABLE 4

Physiological Properties: Part II

| Test Item | Test Result |
|---|---|
| Acid production*¹ |  |
| L-Arabinose | + |
| D-Xylose | + |
| D-Glucose | + |
| D-Mannose | + |
| D-Fructose | + |

TABLE 4-continued

Physiological Properties: Part II

| Test Item | Test Result |
|---|---|
| D-Galactose | + |
| Maltose | + |
| Sucrose | + |
| Lactose | + |
| Trehalose | + |
| D-Sorbitol | + |
| D-Mannitol | + |
| Inositol | + |
| Glycerol | + |
| Starch | − |
| Gas production*² |  |
| L-Arabinose | − |
| D-Xylose | − |
| D-Glucose | − |
| D-Mannose | − |
| D-Fructose | − |
| D-Galactose | − |
| Maltose | − |
| Sucrose | − |
| Lactose | − |
| Trehalose | − |
| D-Sorbitol | − |
| D-Mannitol | − |
| Inositol | − |
| Glycerol | − |
| Starch | − |

*¹As the test medium, the acid production medium disclosed in Gordon, R. E., Haynes, W. C. and Pang, C. H., "The Genus Bacillus" (1973), U.S. Department of Agriculture was used.
*²As the test medium, the gas production medium disclosed in Gordon, R. E., Haynes, W. C. and Pang, C. H., "The Genus Bacillus" (1973), U.S. Department of Agriculture was used.

TABLE 5

Chemotaxonomic Properties

| Test Item | Test Result |
|---|---|
| Major quinone system | MK-7 |

It was also found that the GC content in the intracellular DNA (as determined by HPLC) was 46% by mol.

Based on the results of the morphological observation, physiological character tests and the determination of the GC content in the intracellular DNA so far described, the microorganism was identified referring to Gordon, R. E., Haynes, W. C. and Pang, C. H., "The Genus Bacillus" (1973), U.S. Department of Agriculture and Sneath, P.H.A., Mair, N. S., Sharpe, M. E. and Holt, J. G., "Bergey's Manual of Systematic Bacteriology" Vol. 2, (1986) Williams & Wilkins. As a result, the soil bacterium was identified as a bacterial species belonging to *Bacillus subtilis*. This bacterium was designated *Bacillus subtilis takemi* and deposited at the National Institute of Bioscience and Human-Technology, Agency of Industrial Science and Technology, Ministry of International Trade and Industry (1-3 Higashi 1-Chome, Tsukuba City, Ibaraki Pref., Japan) on Dec. 1, 1998 under the accession number FERM BP-6589. According to the terms of the deposit at the National Institute of Bioscience and Human Technology, all restrictions on the availability to the public of the material so deposited will be irrevocably removed upon the granting of a patent. Bacillus is a group of gram-positive, rod-shaped bacteria that form thermo-stable spores and are distributed widely in common environment such as soil. *Bacillus subtilis* is also known as hay bacillus. In addition to the above-described characters, *Bacillus subtilis takemi* was confirmed to have a remarkable smell of coffee when culture plates of *B. subtilis takemi* cultured as described above were kept in a refrigerator adjusted at about 5° C. Further, it was confirmed that *Bacillus subtilis takemi* contains chitin and/or chitosan in its cell walls.

It should be noted that, not to mention natural and artificial mutants of *Bacillus subtilis takemi*, all of those microorganisms of the genus Bacillus that are capable of reducing nitrates and contain chitin and/or chitosan in their cell walls are included in the present invention.

The microorganism of the invention has preferable properties as a soil microorganism. That is, the microorganism of the invention can reduce nitrates. Also, the chitin matter contained in its cell walls is degraded to chitosan/chitosan oligosaccharides, which in turn react with toxins generated by harmful microorganisms to thereby inhibit the transcription of their DNA to RNA. As a result, the growth of harmful microorganisms is prevented, and damage caused by continuous cropping is reduced. Further, it is convenient to use the microorganism of the invention since its concentration can be judged with its smell of coffee. Therefore, it is possible to improve soil using the microorganism of the invention.

Briefly, the microorganism of the invention and optionally other microorganisms effective for soil improvement are added to an aqueous solution containing nutrients suitable for the growth of the microorganisms. Further, a carrier is added to this solution, which is then agitated. By this operation, the microorganism of the invention is carried by the carrier. The resultant dispersion mixture is maintained within the above-described temperature range appropriate for the growth of the microorganism (e.g. 25–45° C.) to thereby grow the microorganism.

Specific examples of nutrients suitable for the growth of the microorganism of the invention include, but are not limited to, carbon sources such as starch, dextrin, glycerol, glucose, sucrose, galactose, inositol and mannitol; and nitrogen sources such as peptone, soybean powder, meat extract, rice bran, wheat-gluten bread, urea, corn steep liquor, ammonium salts, nitrates, and other organic or inorganic nitrogen compounds. Further, inorganic salts such as table salt, phosphates, metal salts of potassium, calcium, zinc, manganese, iron, etc. may be appropriately added. If necessary, animal oil, vegetable oil, mineral oil or the like may be added as a defoaming agent. A commercially available medium such as Potato Dextrose Agar Medium (product name: NISSUI 05707) may be used. Specific examples of other microorganism effective for soil improvement include, but are not limited to, hydrolase producing microorganisms belonging to the genus Bacillus, Lactobacillus or the like; yeast species belonging to the genus Saccharomyces, Tolura or the like; and filamentous fungi belonging to the genus Aspergillus, Rhizopus or the like. Specific examples of the carrier on which the microorganism of the invention is to be carried include, but are not limited to, porous ceramics, wood pieces, charcoal, straw pieces, and other porous materials on which the microorganism of the invention can survive. The appropriate number of the microorganism cells of the invention per gram of the carrier is $10^2$–$10^{10}$, preferably $10^3$–$10^6$.

A carrier carrying the microorganism of the invention or powder of such a carrier has a function as a soil improving material by itself. However, usually, such a carrier or powder thereof is mixed with raw materials of an organic fertilizer and fermented so that the resultant mixture has both fertilizer effects and soil improvement effects. The carrier carrying the microorganism of the invention or powder thereof may be mixed with organic fertilizer materials at a rate of 2–10 g/kg. For example, powder of a porous ceramic on which the microorganism of the invention has been grown is mixed with bark, poultry droppings and other organic fertilizer materials and then fermented for about 30 days. As the fermentation of the organic materials proceeds, a composition for soil improvement with a high fertilizer response property is obtained which contains microorganisms effective for soil improvement and yet which is rich in chitin and/or chitosan effective as a soil-improving material.

In the application of the above-described composition for soil improvement to soil, 150–600 kg, preferably 220–520 kg of the composition comprising the microorganism of the invention may be applied per 10 a. of farmland (1 a.=100 $m^2$). The composition may be applied at any time from the early growing stage of plants to the harvest stage. The frequency of application is not particularly limited. The time and frequency of the application may be appropriately selected depending on the state of soil and the kind of crops.

It is also possible to treat organic waste by fermentation using the microorganism of the invention. The term "organic waste" used herein refers to waste comprising organic matter, which may be domestic waste, industrial waste or any other waste comprising organic matter. Poultry droppings, cattle droppings and food sludge are also included in this term. Microorganisms are involved in the fermentation and degradation of organic matter. During these processes, bad smells are generated by degradation and by putrefactive microorganisms. Further, offensive odor caused by the growth of putrefactive microorganisms as a result of unbalanced oxygen supply in the fermentation of domestic organic waste, cattle droppings, poultry droppings and food sludge by aerobic bacteria has become a big social problem throughout the country. When organic waste is treated by fermentation using the microorganism of the invention, bad smells can be prevented. Thus, the microorganism of the invention greatly improves the environment. Further, the organic waste that has been treated by fermentation using the microorganism of the invention can be recycled as an organic fertilizer of a high quality.

Preferably, the microorganism of the invention is used in combination with conventional microorganisms used in waste treatment (mainly, aerobic bacilli).

As described above, a carrier (e.g. wood pieces, porous ceramic beads, grains or granules) carrying the microorganism of the invention is prepared and then mixed with organic waste for the purpose of fermentation treatment. The carrier carrying the microorganism of the invention may be used at 2–10 grams per kilogram of organic waste. Specific examples of waste treating microorganisms that may be used in combination with the microorganism of the invention include, but are not limited to, bacteria and filamentous fungi that degrade saccharides contained in waste; aerobic actinomycetes that degrade hemicellulose in waste; anaerobic bacteria that degrade cellulose in waste; and aerobic basidiomycetes that degrade lignin. During the fermentation treatment, it is preferable to provide aeration a rate of 100–200 ml/min per liter of organic waste. Alternatively, air may be supplied by agitation instead of aeration. The temperature may be ambient temperature or may be adjusted at 12–51° C., preferably 25–45° C. In order to improve moisture adjustment and aeration efficiency, auxiliary materials such as wood chips and rice hulls may be added. The period of fermentation treatment varies depending on the composition of the waste to be treated. Usually, this period is 1–30 days, preferably 6–20 days. It is even possible to annihilate organic waste when the above-described fermentation is enhanced by adding a fermentation medium to the waste. If organic waste is considered as a resource and its recovery as a well-balanced fertilizer is desired, the composition of the organic waste may be adjusted by adding thereto cattle droppings, residues from the processing of animal meat or fish meat, etc. The thus treated organic waste becomes an organic fertilizer of a high quality since it comprises chitin and/or chitosan contained in microorganisms.

The results of homology analysis between the 16S ribosomal RNA (16S rRNA) of *Bacillus subtilis takemi* and that of *Bacillus subtilis nattoh* revealed about 93% homology (FIG. 1). *Bacillus subtilis nattoh* is used in the manufacturing of nattoh (fermented soybeans). Nattoh (i.e. fermented soybeans) is known to have an action of lysing clotted blood and, thus, is highly evaluated as a health food. Further, chitin, chitosan or chitosan oligosaccharides, which are metabolites of *Bacillus subtilis nattoh*, are known to play an important role to enhance immunocompetence. However, many people dislike nattoh since it emits an odor of nitrates. Also, production of nitrates results in deterioration of proteins. The microorganisms of the invention including *Bacillus subtilis takemi* have a nitrate-reducing action. Therefore, when soybeans are fermented using the microorganism of the invention, generation of the odor and deterioration of proteins can be prevented. Conventional nattoh has been served as a side dish to cooked rice or the like. On the other hand, the nattoh prepared with the microorganism of the invention has a smell of coffee, and can be taken with bread or used in sandwiches or other western style dishes. As a result, it will become possible to spread nattoh throughout the world as a functional food that is highly nutrient and effective for not only the maintenance of health but also the promotion of health.

Nattoh can be prepared using the microorganism of the invention instead of conventional *Bacillus subtilis nattoh*. Briefly, the microorganism of the invention is added to boiled soybeans and cultured for growth. After the microorganism performed fermentation action, the soybeans are ripened. Methods for preparing nattoh are well known and described, for example, in Susumu Tsuji, "Food Processing Technology Handbook: Revised Edition", pp. 138–143, KENKIN-SHA (1971).

As one application of the above-described method, catechin and ginkgo leaf extract are added to soybeans during the process of preparation of nattoh using the microorganism of the invention. Nattohkinase that lyses clotted blood has an effect of preventing the generation of thrombi or the like; catechin that is anti-microbial has an effect of inhibiting viral growth; and ginkgo leaf extract that is an SOD-like antioxidant has an effect of preventing the generation of active oxygen and improving blood flow in the blood capillary. Since the microorganism of the invention is a nitrate-reducing bacterium, the resultant nattoh has only slight smell of nattoh derived from the odor of ammonium or the like, and yet this slight smell is camouflaged by a smell of coffee. Thus, the resultant nattoh is easy to eat. Besides, an effect of rendering blood vessels strong and an effect of balancing cholesterols in blood vessels that are attributable to the above-described effects can be added to the nattoh. Thus, a completely novel nattoh can be prepared which is effective in preventing diseases of adult people and senile dementia. Although catechin and ginkgo leaf extract have bitterness, the mild taste of the microorganism of the invention reduces their bitterness. Further, it is believed that the microorganism emitting a smell of coffee camouflages their bitterness and the smell peculiar to nattoh.

It is also possible to use the microorganism of the invention as a feed additive. Specific examples of feeds to which the microorganism of the invention may be added include, but are not limited to, feed for domestic animals, fish feed and pet food. For example, when the microorganism of the invention is added to feed for domestic animals, physiological disorders of the animals fed with such feed can be alleviated by the action of the nitrate reductase contained in the microorganism. Besides, the feed conversion ratio in these animals is increased to thereby decrease the calorie of proteins discharged into their droppings. As a result, the offensive odor of droppings is alleviated.

The microorganism of the invention may be added to feed at a rate of $10^3$–$10^6$ cells/g.

It is also possible to use the microorganism of the invention to reduce bitterness of foods, pharmaceuticals, cosmetics and the like. Specific examples of foods having bitterness include, but are not limited to, citrus fruits such as grapefruit, lemon, and juice thereof; vegetables such as tomato, green pepper, celery, and juice thereof; soybean products such as nattoh and soybean milk; fish meat and processed marine products such as ground fish meat; and meat and processed meat products. Specific examples of pharmaceuticals having bitterness include, but are not limited to, catechin and ginkgo leaf extract. Specific examples of cosmetics having bitterness include, but are not limited to, cosmetics applied to the face and cosmetics applied to the oral cavity.

It is contemplated that the microorganism of the invention can be applied in various ways as a food additive. The term "food" used herein includes any and all foods and drinks. Foods to which the microorganism of the invention may be added are not particularly limited. The microorganism may be added, for example, to livestock meat, milk, fishes and shellfishes, and processed products thereof; and cereals, beans, potatoes, vegetables, fruits, and processed products thereof. For example, the microorganism of the invention may be used as a food additive for the preparation of ice cream or yogurt with a smell of coffee. The food additive consisting of the microorganism of the invention has a smell of coffee but contains no caffeine. Thus, the additive has an advantage that it does not form a habit. The microorganism of the invention may be added to food at a rate of $10^3$–$10^6$ cells/g. However, this range may vary depending on the type of food and other factors.

When the microorganism of the invention is coated on a plastic wrapping sheet or inner surfaces of a plastic food container, food wrapped therewith or contained therein can be preserved for a longer period of time without harmful effect on the it, because putrefaction and growth of miscellaneous microorganisms are prevented by the anti-microbial property of chitin and chitosan. The microorganism of the invention may be coated at a rate of $10^1$–$10^5$ cells/cm$^2$ of wrapping sheet or food container. For the coating, live or dead cells of the microorganism of the invention are dispersed in pure water and disrupted by sonication. Then, the resultant dispersion liquid is coated thinly on a wrapping sheet or food container.

In inflammatory sites of patients with atopic dermatitis, staphylococci are growing. It is known that when a paste containing *Bacillus subtilis nattoh* is applied to these sites, *B. subtilis nattoh* eats staphylococci to thereby inhibit the advance of purulence and/or atopy. When the microorganism of the invention is used instead of *B. subtilis nattoh*, the growth of staphylococci is inhibited by the effect of chitin and chitosan in addition to the conventional effect of *B. subtilis nattoh*. Thus, therapeutic effect on atopy is further enhanced. The microorganism of the invention may be formulated into various formulations such as ointment, lotion, cream, paste, gel, emulsion and pack. The content of the microorganism of the invention in such a formulation is not particularly limited; it may be contained at 0.0001–0.1% by weight. The formulation containing the microorganism of the invention may be applied to inflammatory sites of atopic dermatitis patients in a dosage of $10^{-6}$–$10^{-3}$ g (in terms of the microorganism that is the active ingredient) one to several times a day. In the preparation of these formulations, hydrocarbons such as squalane, paraffin and vaseline; oils such as olive oil and almond oil; waxes such as beeswax and lanolin; fatty acids such as stearic acid and oleic acid; higher alcohols such as cetanol and stearyl alcohol; synthetic esters such as glycerol triester; oil phase components such as silicone oil; moisture retentives such as glycerol, propylene glycol, sorbitol and polyethylene glycol; thickning agents such as quince seed gum, pectin and cellulose derivatives; alcohols such as ethanol and isopropyl alcohol; purified water such as deionized water; surfactants such as glycerol monostearate, sorbitan fatty acid ester, fatty acid soap and sodium alkylsulfate; alkali such as potassium hydroxide, sodium hydroxide and triethanolamine; flavoring agents; pigments; chelating agents; preservatives; anti-oxidants; buffers; vitamins; UV absorbents; amino acids and the like may be combined.

BRIEF DESCRIPTION OF THE DRAWINGS

FIG. 1 shows the results of homology analysis between the 16S rRNA of *Bacillus subtilis takemi* and that of *Bacillus subtilis nattoh*. In this Figure, the upper row of the two juxtaposed sequences shows the nucleotide sequence from position 1037 to position 1406 of the 16S rRNA of *Bacillus subtilis takemi,* and the lower row shows the nucleotide sequence of the corresponding region of the 16S rRNA of *Bacillus subtilis nattoh.*

BEST MODES FOR CARRYING OUT THE INVENTION

Hereinbelow, the present invention will be described more specifically with reference to the following Examples, which should not be construed as limiting the scope of the invention.

EXAMPLE 1

Quantitative Determination of Chitin/Chitosan

1. Samples
   1) *Bacillus subtilis takemi*
   2) *Bacillus subtilis nattoh*
2. Outline of the Test Each sample was treated with alkali as described below to obtain insoluble matter, which was subjected to acid hydrolysis and then high performance liquid chromatography to determine the amount of glucosamine. This amount was converted into the amount of chitin (or chitosan).

3. Test Results

The results are shown in Table 6.

TABLE 6

| | Test Results | |
|---|---|---|
| | Chitin/Chitosan (%) | |
| Sample | In terms of chitin | In terms of chitosan |
| 1) | 0.044 | 0.035 |
| 2) | Not detected | Not detected |

Detection limit: 0.001%

4. Testing Method
   1) Alkali Treatment

About 5 g of the sample was weighed accurately. Five milliliters of 8% (w/v) sodium hydroxide solution was added thereto, and the resultant mixture was heated for 2 hours in boiling water bath. After cooled to room temperature, the mixture was vacuum filtered with a membrane filter (0.45 μm). The residue was washed with water until the filtrate became neutral.

2) Acid Hydrolysis

The residue was dried overnight at 60° C. together with the membrane filter. Then, the residue was transferred into a test tube to be sealed. Five milliliters of 6 mol/L hydrochloric acid was added to the test tube, which was then sealed under reduced pressure and placed in a dryer at 100° C. for 16 hours for hydrolysis. After cooled to room temperature, the resultant hydrolysate was condensed and dried to solid with a rotary evaporator to thereby remove hydrochloric acid. The residue was dissolved in a small volume of water and then neutralized with a sodium hydroxide solution. Water was added thereto to make the total volume 10 ml. This solution was filtered with a membrane filter (0.45 μm) to obtain the filtrate as a test solution, which was then applied to high performance liquid chromatography after appropriate dilution.

3) Quantitative Determination of Glucosamine

The amount of glucosamine in the test solution was quantitatively determined by high performance liquid chromatography (absolute calibration curve method, measurement of peak height).

4) Calculation i) When the determined glucosamine was converted into chitin (N-acetylglucosamine polymer):
   Chitin (%) = $G \times V/W \times 10^{-4} \times 1.1341$
   G: glucosamine concentration (μl/ml) in the test solution determined from the calibration curve
   V: constant volume of the test solution (ml)
   W: amount of the sample used (g)
   1.1341: weight conversion factor from glucosamine to chitin ii) When the determined glucosamine was converted into chitosan (glucosamine polymer):
   Chitosan (%) = $G \times V/W \times 10 - 4 \times 0.8995$
   G: glucosamine concentration (μl/ml) in the test solution determined from the calibration curve
   V: constant volume of the test solution (ml)
   W: amount of the sample used (g)
   0.8995: weight conversion factor from glucosamine to chitosan

EXAMPLE 2

Preparation of a Composition for Soil Improvement

A granule-type inorganic porous ceramic that releases 88 kinds of anions and cations was provided (product name: Z Gold; manufactured by Gold Kousan Co., Ltd.). To 1,200 ml of an aqueous solution containing 120 g of glucose and 60 g of yeast extract, 3 kg of the above inorganic, porous ceramic granules was added and agitated thoroughly. To this mixture, 300 ml of a liquid containing *Bacillus subtilis takemi* at $1 \times 10^8$ cells/ml was added and agitated. The resultant dispersion mixture was maintained at 25–45° C. to thereby grow the microorganism in the pores of the porous ceramic.

The resultant ceramic granules were powdered, and then mixed with an organic fertilizer material consisting of 200 kg of rape seed meals, 200 kg of bone dust, 150 kg of fish cake, 150 kg of rice bran, 100 kg of soybean powder, 100 kg of poultry droppings and 100 kg of seaweed compost. This mixture was fermented for about 30 days. As the fermentation of organic matter proceeded, a composition for soil improvement with a high fertilizer response property was obtained which contained not only microorganisms effective for soil improvement but also plenty of chitin and/or chitosan that are effective as a soil improving material.

EXAMPLE 3

Tomato Cultivation Using the Composition for Soil Improvement

Tomato is a representative vegetable that dislikes continuous cropping. Damage by continuous cropping is believed to occur because of the following reasons. Briefly, as a result of abundant application of agricultural chemicals and fertilizers, root hairs of plants are burnt and become incapable of absorbing phosphor and minerals; useful microorganisms in soil are killed and thus the food-chain between useful microorganisms and plants is inhibited; and harmful microorganisms propagate to cause diseases.

Thirty to thirty-five bags of the composition for soil improvement (prepared in Example 2 above) (15 kg/bag) was applied per 10 a. of tomato cultivating field.

As a result, tomato plants grown up there had appropriate heights and were sturdy with short internodes. Usually, flower bud growth tends to become unfavorable at the 3rd and 4th branch joints. However, such a problem was not observed in the tomato plants grown in this Example. A yield 20–30% higher than the conventional yield was achieved. Furthermore, in spite of the fact that occurrence of diseases and considerable decrease in yield are frequently observed in the second year of continuous cropping, no damage by continuous cropping was observed for 4 years and a good yield could be secured in this Example.

When these tomato plants were pulled out from soil, it was observed that their roots were spreading sufficiently and that root hairs were grown up well.

EXAMPLE 4

Preparation of a Fermentation Material to Treat Organic Waste

A granule-type inorganic porous ceramic that releases 88 kinds of anions and cations was provided (product name: Z Gold; manufactured by Gold Kousan, Co., Ltd.). To 1,200 ml of an aqueous solution containing 120 g of glucose and 60 g of yeast extract, 3 kg of the above inorganic, porous ceramic granules was added and agitated thoroughly. To this mixture, 300 ml of a liquid containing *Bacillus subtilis takemi* at $1 \times 10^8$ cells/ml was added and agitated. This dispersion mixture was maintained at 25–45° C. to grow the microorganism in the pores of the porous ceramic.

EXAMPLE 5

Fermentation Treatment of Organic Waste

Organic waste was treated by fermentation using a vertical-type garbage (i.e. wet waste from kitchens) fermentation apparatus (product name: Takemi Type Garbage Fermentation Apparatus Model 6; manufactured by Gold Kousan Co., Ltd.).

This apparatus has a vertical shape and is composed of 3 fermenters piled up, each of them being 600 mm in inside diameter and 600 mm in height. The top layer is an inlet for garbage, and the 2nd and 3rd layers are fermenters. This apparatus can treat 50–100 kg of garbage per day continuously. This apparatus is designed so that the fermenter at each layer can be rotated independently. Besides, each layer is provided with a rotary blade for the purposes of agitation and disruption of garbage. Each fermenter is designed so that intake/exhaustion of air can be performed independently. Also, the fermenter is covered with a heat insulator so that temperature control can be performed independently.

The fermentation material prepared in Example 4 above was put in advance in the fermenter at the top layer. Generally, the amount of the fermentation material put therein is 50 kg, which enables continuous operation for 1 to 5 years without supplementation though some decrease would occur because of abrasion or the like. Garbage from food industry or households was put into this fermenter from an inlet provided at the upper part thereof. While rotating the fermenter, air was fed thereto, and the fermenter was heated to 35–45° C. As a result, the ferment microorganism in the fermentation material grew and the fermentation of the garbage started. Prior to the treatment, the composition of garbage was adjusted by adding thereto droppings from domestic animals, residues from the processing of animals and fishes, etc.

As time passed on, the garbage moved to the 2nd layer and then to the 3rd layer with fermentation progressing. Finally, the garbage was taken out from the bottom of the 3rd fermenter as a high quality fertilizer.

Since *Bacillus subtilis takemi* is a nitrate-reducing microorganism, it does not generate offensive odor attributable to ammonia, and yet it has a smell of coffee. Besides, discharged material from this microorganism serves as a fertilizer and, at the same time, as a high quality soil-improving material containing chitin and/or chitosan.

EXAMPLE 6

Soybeans (1 kg) were washed and dipped in a sufficient volume of water for half a day. Soybeans that had absorbed enough water were steamed until they could be easily crushed with the thumb and the index finger.

Two loopfuls of *Bacillus subtilis takemi* dissolved in 2 tablespoonfuls of hot water was poured over the steamed soybeans quickly so that the microorganism was distributed uniformly while the soybeans were still hot.

The soybeans were placed flatly in a dish so that they had a height of about 2 cm and could contact air.

This dish was put in an incubator adjusted at around 42° C. and incubated for one to two days. Then, a white membrane appeared on the surfaces of the soybeans. Thus, nattoh was obtained. When this nattoh was cooled in a refrigerator, it was further ripened and presented a good taste.

The thus obtained nattoh gave the same touch to the teeth as conventional nattoh, but it did not have the smell of ammonia peculiar to conventional nattoh since *Bacillus subtilis takemi* is a nitrate-reducing microorganism. Besides, this nattoh had a smell of coffee peculiar to the microorganism. As a result, it has become a food that is acceptable to those who dislike conventional nattoh and is suitable as a side dish to not only cooked rice but to other foods.

EXAMPLE 7

| Preparation of a Feed Additive | |
|---|---|
| Components | |
| Humus soil | 30% |
| Yeast extract | 18% |
| Z Gold | 15% |
| Natural antimicrobial materials (Hinokitiol, Brazil Pure Propolis) | 10% |
| Natural organic acids (mixture of malic acid, acetic acid, citric acid and kojic acid) | 7% |
| Emulsified oligosaccharides | 5% |
| Natural vitamin C | 5% |
| Dispersion liquid of useful microorganisms* (total $10^8$ cells/L) | 10% |

*: *Enterococcus faecium, Lactobacillus acidophilus, Bifidobacterium bifidum*

"P-17 Z Gold" (a porous ceramic of which the major component is natural calcium; a product manufactured by Gold Kousan Co., Ltd.) was treated in the same manner as described in Example 4 to thereby grow *Bacillus subtilis takemi*. The resultant ceramic was crushed into powder 1 mm or less in size so that domestic animals could eat without any trouble. To this powder, the above-described components were added at the indicated ratios, agitated and then maintained at 35–45° C. for fermentation. Fermentation conditions were adjusted so that $10^3$–$10^6$ cells were contained per gram of the feed.

EXAMPLE 8

Feeding of the Feed Additive

The feed additive prepared in Example 7 above was added to feeds for domestic animals at the ratios indicated below.

Cattle: 0.4%, Pig: 0.6%, Chicken: 0.3–0.4%

Fifteen healthy pigs and 15 weak pigs were selected from a group of young pigs born almost at the same time in the same pig farm. On day 75 after birth, they began to receive a feed to which the above feed additive had been added at 0.6%.

On day 75, the average body weight of the weak group was 3 kg lower than that of the healthy group. On day 175, difference in average body weight between the test group and the control group became zero. At the time of shipment on day 200, the average body weight of the test group in the weak group was 2.8 kg higher than that of the control group.

In the internal organs of the pigs in the test groups, neither jaundice symptoms nor cardiac hypertrophy was observed. The melting point of their fat was 3.2° C. higher than that of the control pigs; their fat was a high quality fat containing less unsaturated fatty acids that would generate active oxygen. The emission of offensive odor from droppings was also reduced in the test groups.

EXAMPLE 9

Dry soybeans (1 kg) were steamed. Catechin (15–30 g; manufactured by Ito En, Ltd.) and ginkgo leaf extract (15–30 g; manufactured by TAMA BIOCHEMICAL Co., Ltd.) were added to the steamed soybeans. Then, nattoh was prepared in the same matter as described in Example 6.

When compared to conventional nattoh supplemented with catechin and ginkgo leaf extract, the nattoh of this Example prepared in the same manner as Example 6 with the addition of catechin and ginkgo leaf extract had a remarkably reduced smell of nattoh. Also, the bitterness of catechin and ginkgo leaf extract was reduced in the nattoh of this Example.

EXAMPLE 10

A formulation containing *Bacillus subtilis takemi* was prepared according to the following prescription.

| Cream | |
|---|---|
| *Bacillus subtilis takemi* | $10^9$–$10^{12}$ cells |
| Stearyl alcohol | 6.0 g |
| Stearic acid | 2.0 g |
| Hydrogenated lanolin | 4.0 g |
| Squalane | 9.0 g |
| Octyldodecanol | 10.0 g |
| 1,3 butylene glycol | 6.0 g |
| PEG 1500 | 4.0 g |
| POE(25) cetyl alcohol ether | 3.0 g |
| Glycerol monostearate | 2.0 g |
| Purified water* | 54.0 g |

*Mineral <<88>> (a solution manufactured by Gold Kousan Co., Ltd. containing 88 kinds of mineral anions and cations)

EXAMPLE 11

A formulation containing *Bacillus subtilis takemi* was prepared To 1 of milk, 15 ml of an instant yogurt mix and 1 g of the inorganic porous ceramic granules (1–10 μm in average particle size) carrying *Bacillus subtilis takemi* prepared in Example 4 were added and mixed thoroughly. The resultant mixture was incubated at about 30° C. for 3–6 hours to thereby yield a yogurt.

A formulation containing *Bacillus subtilis takemi* was prepared The thus prepared yogurt was less sour because of the effect of *Bacillus subtilis takemi;* more nutritious with chitin and chitosan oligosaccharides contained therein; and had a smell of coffee. Thus, it was a yogurt good for health and easy-to-take.

EXAMPLE 12

A formulation containing *Bacillus subtilis takemi* was prepared A liquid containing *Bacillus subtilis takemi* grown was centrifuged and the supernatant was discarded. Pure water was added to the precipitate, which was subjected to dispersion washing and then centrifuged again. These operations were repeated 5 times. The final precipitate was dispersed in pure water to give a concentration of $1\times10^9$–$1\times10^{11}$ cells/ml.

A formulation containing *Bacillus subtilis takemi* was prepared This dispersion liquid was sonicated to disrupt cells. The thus prepared liquid containing disrupted cells was put in a sprayer and sprayed onto a wrapping sheet of vinyl chloride or the like. After sufficiently dried, the sheet was rolled. One milliliter of the dispersion liquid was sprayed per $m^2$. These series of operations were carried out in an aseptic room to avoid contamination with miscellaneous microorganisms.

A formulation containing *Bacillus subtilis takemi* was prepared To the thus prepared wrapping sheet and a commercial wrapping sheet just unsealed, 0.1 ml of *E. coli* culture liquid containing $10^6$ cells/ml was dropped and left at 30° C. for 8 hours. As a result, *E. coli* grew and formed colonies on the commercial wrapping sheet. On the other hand, no colony formation was observed on the wrapping sheet that had been coated with *Bacillus subtilis takemi.* Thus, it was confirmed that this microorganism has anti-microbial property.

When a water containing anti-microbial titanium ions, silver ions, germanium ions, cobalt ions, neodymium ions, etc. is used as dispersion liquid of disrupted *Bacillus subtilis takemi,* anti-microbial property is further enhanced.

All the publications, patents and patent applications cited in the present specification are incorporated herein by reference in their entireties.

INDUSTRIAL APPLICABILITY

The microorganism of the invention is useful since it can be used for improving soil, for treating organic waste by fermentation, for fermenting soybeans, and for reducing bitterness. The microorganism of the invention can also be used as a feed additive or a food additive. Further, the microorganism of the invention has an anti-microbial effect.

What is claimed is:

1. A biologically pure culture of microorganism *Bacillus subtilis takemi* having deposit No. FERM BP-6589, which is capable of reducing nitrates, contains chitin and/or chitosan in its cell walls and has a smell of coffee.

2. A composition for improving soil comprising the microorganism of claim 1.

3. A composition for treating organic waste through fermentation comprising the microorganism of claim 1.

4. A feed additive comprising the microorganism of claim 1.

5. A composition for reducing bitterness comprising the microorganism of claim 1.

6. A food additive comprising the microorganism of claim 1.

* * * * *

SEQUENCE LISTING

<160> NUMBER OF SEQ ID NOS: 2

<210> SEQ ID NO 1
<211> LENGTH: 326
<212> TYPE: DNA
<213> ORGANISM: Bacillus subtilis
<220> FEATURE:
<221> NAME/KEY: misc_feature
<222> LOCATION: (1)..(326)
<223> OTHER INFORMATION: n is any nucleotide

<400> SEQUENCE: 1

| | | | | | |
|---|---|---|---|---|---|
| gagatgttgg | ttaagtcccg | cgacgaggcn | acccttgtnt | nagtngccag | caattcagtn | 60 |
| ggcantntaa | agtgactgcc | gtgacaagcc | ggaggaaagg | tgggaatgac | gtcaaatcat | 120 |
| catgcccta | tacgacntgg | gctacacacg | tgctaccatg | gacagaacaa | agggcagcga | 180 |
| aaccgcgagg | ttaagccaat | cccacaaatc | tgttctcagt | tcggatcgca | gtntgcaact | 240 |
| tcgactgcgt | gaagctggaa | tcgctagtaa | tcgcggatca | gcatgccgcg | gtgaatacgt | 300 |
| tcccgggcct | tgtacacacc | gcccgt | | | | 326 |

<210> SEQ ID NO 2
<211> LENGTH: 327
<212> TYPE: DNA
<213> ORGANISM: Bacillus subtilis

<400> SEQUENCE: 2

| | | | | | |
|---|---|---|---|---|---|
| gagatgttgg | gttaagtccc | gcaacgagcg | caacccttga | tcttagttgc | cagcattcag | 60 |
| ttgggcactc | taaggtgact | gccggtgaca | aaccggagga | aggtgggat | gacgtcaaat | 120 |
| catcatgccc | cttatgacct | gggctacaca | cgtgctacaa | tggacagaac | aaagggcagc | 180 |
| gaaaccgcga | ggttaagcca | atcccacaaa | tctgttctca | gttcggatcg | cagtctgcaa | 240 |
| ctcgactgcg | tgaagctgga | atcgctagta | atcgcggatc | agcatgccgc | ggtgaatacg | 300 |
| ttcccgggcc | ttgtacacac | cgcccgt | | | | 327 |